United States Patent
Hotta et al.

(10) Patent No.: US 8,609,235 B2
(45) Date of Patent: Dec. 17, 2013

(54) POROUS CERAMIC MATERIAL AND METHOD OF PRODUCING THE SAME

(75) Inventors: Yuji Hotta, Kurashiki (JP); Yasushi Suetsugu, Tsukuba (JP); Masanori Kikuchi, Tsukuba (JP); Toshiyuki Ikoma, Tsukuba (JP); Tomoya Kuwayama, Kurashiki (JP); Takashi Makabe, Kurashiki (JP); Junzo Tanaka, Tsukuba (JP)

(73) Assignees: Kuraray Co., Ltd., Kurashiki-shi (JP); National Institute for Materials Science, Tsukuba-shi (JP)

( * ) Notice: Subject to any disclaimer, the term of this patent is extended or adjusted under 35 U.S.C. 154(b) by 593 days.

(21) Appl. No.: 12/306,341

(22) PCT Filed: Jun. 22, 2007

(86) PCT No.: PCT/JP2007/062602
§ 371 (c)(1),
(2), (4) Date: Jan. 5, 2009

(87) PCT Pub. No.: WO2007/148788
PCT Pub. Date: Dec. 27, 2007

(65) Prior Publication Data
US 2009/0281633 A1 Nov. 12, 2009

(30) Foreign Application Priority Data
Jun. 23, 2006 (JP) ................................. 2006-174372

(51) Int. Cl.
*B32B 3/26* (2006.01)
*A61F 2/28* (2006.01)

(52) U.S. Cl.
USPC ..................... 428/304.4; 428/314.2; 428/702; 623/23.56

(58) Field of Classification Search
None
See application file for complete search history.

(56) References Cited

U.S. PATENT DOCUMENTS

| 5,141,510 A | 8/1992 | Takagi et al. |
| 5,228,571 A | 7/1993 | Anderson |

(Continued)

FOREIGN PATENT DOCUMENTS

| JP | 2001 192280 | 7/2001 |
| JP | 3470759 | 9/2003 |
| JP | 2003-335574 | 11/2003 |
| JP | 2004 275202 | 10/2004 |
| JP | 2004-275202 | 10/2004 |
| JP | 2005 1943 | 1/2005 |

OTHER PUBLICATIONS

Office Action mailed Aug. 9, 2011, in co-pending U.S. Appl. No. 12/678,096.

*Primary Examiner* — David Sample
(74) *Attorney, Agent, or Firm* — Oblon, Spivak, McClelland, Maier & Neustadt, L.L.P.

(57) ABSTRACT

Provision of a porous ceramic material which rapidly induces bone tissue formation and has practical strength.
A porous ceramic material 11 having substantially unidirectionally oriented pores 12, a porosity of 40-90%, and an average open area of one pore of $0.05 \times 10^{-3}$-$50 \times 10^{-3}$ mm$^2$ both in a first sectional surface perpendicular to the pore 12 orientation direction and a second sectional surface parallel to the first sectional surface and 5 mm distant from the first sectional surface in the pore 12 orientation direction. Using the material 11, when a cylindrical test piece (diameter 3 mm×height 5 mm, the pore 12 array direction as a height direction) made of the material is dipped in polyethylene glycol up to 1 mm from one end thereof, polyethylene glycol permeates through the whole test piece preferably within 30 seconds.

14 Claims, 7 Drawing Sheets

1 1  porous ceramic material
1 2  pore

(56) References Cited

U.S. PATENT DOCUMENTS

| | | | |
|---|---|---|---|
| 5,531,794 A * | 7/1996 | Takagi et al. | 623/23.56 |
| 6,187,329 B1 | 2/2001 | Agrawal et al. | |
| 6,905,516 B1 * | 6/2005 | Lemaitre et al. | 623/23.56 |
| 2004/0162622 A1 | 8/2004 | Simon et al. | |
| 2004/0230303 A1 | 11/2004 | Gomes et al. | |
| 2004/0253185 A1 | 12/2004 | Herweck et al. | |
| 2007/0282455 A1 | 12/2007 | Luginbuehl et al. | |
| 2008/0226893 A1 * | 9/2008 | Yang et al. | 428/312.2 |
| 2009/0281633 A1 | 11/2009 | Hotta et al. | |
| 2010/0234966 A1 * | 9/2010 | Lo | 623/23.51 |

\* cited by examiner 1 1 porous ceramic material
1 2 pore (A)

(B)

POROUS CERAMIC MATERIAL AND METHOD OF PRODUCING THE SAME

TECHNICAL FIELD

The present invention relates to a porous ceramic material and a production method thereof.

BACKGROUND ART

Among the ceramic materials calcium phosphate ceramic material is a main component of bone and tooth, has superior biocompatibility, and is superior in the safety. Therefore, it is widely known as a medical material such as artificial bone, artificial dental root and the like, or biomaterials such as dental cement and the like.

Among these, the research and development are actively performed in recent years of ceramic materials suitable for an artificial bone used for repairing or healing by filling in a defect or hole made in the bone die to a disease such as bone fracture, bone tumor and the like or a treatment thereof. Although ceramic materials are already used widely in the clinical practice, current ceramic materials are defective in that the new bone formation after embedding into an affected part is limited to the surface layer of the material and the strength is not sufficient, thereby prolonging the time necessary for healing the injury.

Accordingly, the development of a ceramic implant material, which allows a biological tissue to rapidly penetrate the inside and quickly form a tissue (new bone), and has a practical strength, is desired.

As such ceramic implant material, (1) calcium phosphate sintered body wherein many pores are densely distributed three-dimensionally, and a skeleton wall compartmentalizing adjacent pores has linked sphere-like opened pores communicating with them (see patent document 1), (2) a method of forming bead-shaped porous ceramic materials having pores by connecting them with a nylon wire and the like (see patent document 2) and the like are suggested.

Moreover, it is disclosed that a sintered body having unidirectionally-oriented pores with a diameter of 10-500 μm is a ceramic material suitable as an implant material (see patent document 3).
patent document 1: JP-B-3470759
patent document 2: JP-A-2003-335574
patent document 3: JP-A-2004-275202

DISCLOSURE OF THE INVENTION

Problems to be Solved by the Invention

However, the method of patent document 1 fails to lead a bone tissue (new bone) in clinical practice, since the interpore connection consisting of linked spherical opened pores has a small pore size and is free of orientation. In the method of patent document 2, the material shrinks during sintering. Therefore, an implant material with a desired size cannot be obtained without re-forming after sintering. As a result, the step becomes complicated and the method has low practicality since it includes connecting many beads with a nylon wire and the like.

Although patent document 3 suggests a preferable embodiment of a material for implant, it was clarified according to the test by the present inventors that the method of the document cannot produce an implant material with a sufficiently long oriented continuous pore. Consequently, it was found that patent document 3 cannot be a specific or practical guidance for a material which allows quick permeation of blood or bone marrow fluid thereinto.

The present invention has been made in view of the above-mentioned problems, and an object thereof is to provide a porous ceramic material that rapidly leads bone tissue formation and having a practical strength.

Means of Solving the Problems

The present inventors have conducted intensive studies in an attempt to solve the above-mentioned problem and completed the present invention having the following characteristics. (1) A porous ceramic material having substantially unidirectionally oriented pores in its inside, wherein when a cylindrical test piece (diameter 3 mm×height 5 mm, the pore orientation direction as a height direction) made of the material is dipped in polyethylene glycol up to 1 mm from one end thereof, polyethylene glycol permeates through the whole test piece within 30 seconds.
(2) A porous ceramic material having (a) substantially unidirectionally oriented pores, (b) a porosity of 40-90%, and (c) an average cross sectional area of one pore of $0.05 \times 10^{-3}$-$50 \times 10^{-3}$ mm$^2$ both in a first sectional surface perpendicular to the pore orientation direction and a second sectional surface parallel to the first sectional surface and 5 mm distant from the first sectional surface in the pore orientation direction.
(3) A porous ceramic material having substantially unidirectionally oriented pores in its inside and a cross sectional area (perpendicular to the orientation direction) of the pores of $0.05 \times 10^{-3}$-$100 \times 10^{-3}$ mm$^2$ at least for a 5 mm length in the orientation direction.
(4) The porous ceramic material of (3), wherein the porosity is 40-90%.
(5) The porous ceramic material of any of (1) to (4), comprising calcium phosphate as a main component.
(6) The porous ceramic material of (5), wherein calcium phosphate is hydroxyapatite and/or tricalcium phosphate.
(7) A porous ceramic implant material comprised of a porous ceramic material of any of (1) to (6).
(8) A method of producing a porous ceramic material, comprising
step (A): a step of preparing a slurry by dispersing a ceramic starting material in water,
step (B): a step of filling a slurry in a given container, and cooling one end of the slurry container to unidirectionally freeze the slurry from the end side,
step (C): a step of drying the frozen slurry to give a green body, and
step (D): a step of sintering the green body,
wherein the circumference of the slurry container except the above-mentioned one end is cooled in step (B) to a temperature higher than the coagulation point of the slurry.

Effect of the Invention

The present invention provides a porous ceramic material, which allows blood or bone marrow fluid to smoothly permeate through its inside, has a high compressive strength in the direction thereof and a bending strength in the direction perpendicular thereto, and is particularly suitable for artificial bone and the like.

Figure 1:
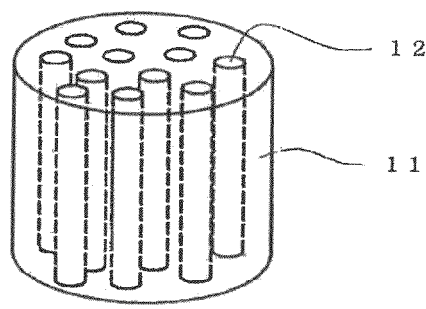
FIG. 1 is a schematic diagram of the porous ceramic material of the present invention.

EXPLANATION OF SYMBOLS 11 porous ceramic material
12 pore
21 slurry
31 container
41 sample table
51 particles of ceramic starting material
61 ice
62 pore

BEST MODE FOR CARRYING OUT THE INVENTION

The porous ceramic material of the present invention is explained in the following. In the following description, the porous ceramic material of the present invention is also simply indicated as the material of the present invention.

The porosity of the material of the present invention is preferably 40-90%, more preferably 50-90%, further preferably 60-90%. When the porosity is not less than 40%, sufficient bone formation is expected, since much blood, bone marrow fluid and the like permeate into the material. When the porosity is not more than 90%, the porous ceramic material is highly strong.

The porosity is measured in conformity to JIS R 1634. Specifically, the following is performed. A diameter 3 mm×height 5 mm cylindrical test piece is cut out from an evaluation target porous ceramic material. The weight and volume of the test piece are measured and the porosity is calculated according to the following formulas.

bulk density=(weight of sample)/(volume of sample)

porosity=(1−bulk density/3.16)×100

FIG. 1 is a schematic diagram of the porous ceramic material of the present invention. In the material of the present invention, pores 12 are unidirectionally oriented as shown in FIG. 1. The pore 12 is a region of an empty space without a ceramic substance inside a ceramic material 11. The pores being unidirectionally arrayed means that pores extending in the uniaxial direction are present and the long axis direction of such pores is arranged to be substantially unidirectional. More specifically, for example, the long axis direction of not less than half, preferably not less than 80%, of the pores extending in the uniaxial direction in the ceramic material is arranged to fall, for example, within the range of 30°.

The cross sectional area (perpendicular to the orientation direction) of each pore is preferably $0.05 \times 10^{-3}$-$100 \times 10^{-3}$ mm$^2$, more preferably $0.05 \times 10^{-3}$-$50 \times 10^{-3}$ mm$^2$.

The above-mentioned range is a sufficient size to be permeated by the blood and bone marrow fluid, at which the blood and bone marrow fluid can easily pass by the capillary action. To solve the problem of the present invention, however, it is not necessary for all pores in the material to have the above-mentioned cross sectional area. In addition, for the cell etc. contained in the blood, bone marrow fluid and the like to penetrate into a porous ceramic material, a pore in the cross section perpendicular to the orientation direction has a minor axis of at least 10 μm, preferably 20 μm, more preferably not less than 30 μm.

The length of the pore in the long axis direction is preferably not less than 5 mm, more preferably not less than 7 mm, still more preferably not less than 10 mm. The length does not have a particular upper limit. When the pore has a sufficient length, an implant material can be obtained easily by cutting etc. To solve the problem of the present invention, however, it is not necessary for all pores in the material to have the above-mentioned length.

In a preferable embodiment, a pore has a cross sectional area perpendicular to the orientation direction of $0.05 \times 10^{-3}$-$100 \times 10^{-3}$ mm$^2$, more preferably $0.05 \times 10^{-3}$-$50 \times 10^{-3}$ mm$^2$, for at least 5 mm length in the orientation direction. In this case, good permeation of blood, bone marrow fluid and the like can be achieved for a practically sufficient length. It is not necessary for all pores in the material to have the above-mentioned cross sectional area.

To determine the cross sectional area of a pore, a porous ceramic material to be measured is embedded in a resin, this is cut perpendicularly to the oriented axial direction and observed with a microscope and the like, and open areas formed by the pores are successively measured. At this time, the material is cut out every 1 mm and the open areas in each cross section are measured, whereby the shift, along the orientation length direction of the pores, of the cross sectional area of the pores can be evaluated with a precision suitable for the object of the present invention.

As mentioned above, when the material is cut out every 1 mm in the pore orientation direction and the open area of the pores in the obtained thin section is measured, the ratio of the maximum open area to the minimum open area in a 5 mm length (that is, successive 5 thin sections) where the change in the amount of open area of the pores is the smallest is preferably within 10-fold, more preferably within 5-fold. Thus, as an implant material, the open area derived from the pores, namely, the cross sectional area of the pores, preferably shows smaller variation along the pore orientation direction, since permeation of blood, bone marrow fluid and the like into the material due to the capillary action becomes smooth. That is, when the material is cut out every 1 mm in the pore orientation direction and the cross sectional area of the pores in the obtained thin section is measured, the ratio of the maximum cross sectional area to the minimum cross sectional area in a 5 mm length (that is, successive 5 thin sections) where the change in the amount of open area of the pores is the smallest is preferably within 10-fold, more preferably within 5-fold. As an implant material, the cross sectional area of the pores preferably shows smaller variation along the pore orientation direction, since permeation of blood, bone marrow fluid and the like into the material due to the capillary action becomes smooth. Furthermore, when the ratio is within the range mentioned above, a porous ceramic material having a superior strength can be provided since ceramic layers are arrayed almost in parallel to each other.

In the porous ceramic material, a first sectional surface perpendicular to the pore orientation direction, and a second sectional surface parallel to the first sectional surface and 5 mm distant in the pore orientation direction from the first sectional surface are focused on. Preferably, an opening (cross section of pore) having an opening area (cross sectional area) of $0.05 \times 10^{-3}$-$100 \times 10^{-3}$ mm$^2$ is present in both the first sectional surface and the second sectional surface. When the open area and its frequency are within preferable ranges in both the first sectional surface and the second sectional surface, preferable pores are considered to be present inside the material. More preferably, an opening (cross section of pore) having an opening area (cross sectional area) of $0.05 \times 10^{-3}$-$50 \times 10^{-3}$ mm$^2$ is present in both the first sectional surface and the second sectional surface.

Preferably, in both the aforementioned first sectional surface and second sectional surface, an average value of the open area of the pore (that is, cross sectional area of pore) is $0.05 \times 10^{-3}$-$50 \times 10^{-3}$ mm$^2$, more preferably $0.05 \times 10^{-3}$-$30 \times 10^{-3}$ mm$^2$. To determine the average value, a porous ceramic material is embedded in a resin, this is cut perpendicularly to the oriented axial direction and observed with a microscope, the opening area of pores (cross sectional area of pores) in a 0.7 mm square is measured, and the average value of the opening area of pores (cross sectional area of pores) is obtained.

From another aspect, the material of the present invention can be defined by the permeability of polyethylene glycol. Since polyethylene glycol (average molecular weight about 600) has liquid property similar to that of blood, bone marrow fluid and the like, it is preferable as a model of blood, bone marrow fluid and the like. Since polyethylene glycol has a viscosity higher than that of blood, permeation of polyethylene glycol into the material means permeation of blood into the inside of the ceramic material. A specific evaluation method is as follows. A diameter 3 mm×height 5 mm cylindrical test piece is cut out from a porous ceramic material. At this time, the direction in the material is the height direction of the test piece. The test piece is dipped in polyethylene glycol up to 1 mm from one end at room temperature. The time up to visual observation of permeation of polyethylene glycol in the whole test piece is measured. To facilitate observation of the permeation, a dye and the like may be dissolved in polyethylene glycol. Preferably, polyethylene glycol permeates into the whole test piece within 30 sec, more preferably within 20 sec.

Next, the composition and the production method of the porous ceramic material are explained.

Figure 2:
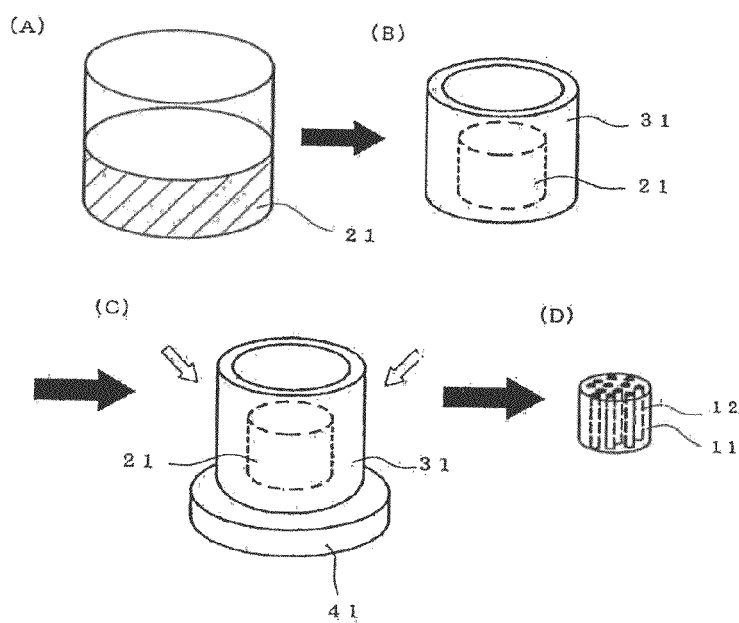
FIG. 2 shows one example of the production method of the porous ceramic material of the present invention.

FIG. 2 shows one example of the production method of the porous ceramic material of the present invention.

As shown in FIG. 2, the production method of the material of the present invention has a slurry preparation step including dispersing a ceramic starting material in water (step A), a freezing step including growing needle-like ice by freezing the obtained slurry from one direction (step B), a drying step including lyophilizing the frozen slurry in vacuum to sublimate the ice, thus forming a green body having macropores (step C), and a sintering step wherein by a heat treatment, the green body after sublimation of ice to form micropores in the ceramic wall (step D).

The production method of this embodiment is explained in the following according to each step.

FIG. 2(A) schematically shows preparation of a slurry. Slurry 21 to be used for step A can be prepared by dispersing the ceramic starting material in water. Here, the "ceramic starting material" refers to particles used for producing the ceramic material, preferably particles used for producing calcium phosphate ceramic materials. In addition, the below-mentioned additives are preferably dissolved or dispersed in slurry 21.

As the ceramic starting material, calcium phosphate is preferable. In other words, to obtain a calcium phosphate ceramic material (that is, a ceramic material comprising calcium phosphate as a main component) in the present invention, the ceramic starting material is preferably calcium phosphate in its entirety. When particles other than calcium phosphate are used, the amount to be used thereof is not more than 25 wt % of the total ceramic starting material.

Examples of calcium phosphate include hydroxyapatite, fluorapatite, chlorapatite, tricalcium phosphate, calcium metaphosphate, tetracalcium phosphate, calcium hydrogen phosphate, calcium hydrogen phosphate dihydrate and the like. In the material of the present intention, a part of Ca component of calcium phosphate may be substituted by one or more kinds selected from Sr, Ba, Mg, Fe, Al, Y, La, Na, K, Ag, Pd, Zn, Pb, Cd, H and other rare earths. In addition, a part of ($PO_4$) component may be substituted by one or more kinds selected from $VO_4$, $BO_3$, $SO_4$, $CO_3$, $SiO_4$ and the like. Furthermore, a part of (OH) component may be substituted by one or more kinds selected from F, Cl, O, $CO_3$, I and Br.

For bone formation, calcium phosphate is more preferably hydroxyapatite, fluorapatite, chlorapatite or tricalcium phosphate, most preferably apatite hydroxide or tricalcium phosphate. Calcium phosphate may be derived from natural mineral, or may be synthesized by various wet processes, dry processes and the like.

Examples of the ceramic starting material other than calcium phosphate include titania, zirconia, alumina, magnesia, silicon carbide and the like.

The ceramic starting material undergoes the below-mentioned steps B-D to afford a ceramic sintered body wherein sintered layers of ceramic particles and pores are unidirectionally oriented. For implant use of the porous ceramic material of the present invention, for example, a dense, sintered layer of ceramic particles is preferably formed to secure practical strength. Hence, the ceramic starting material to be used for slurry 21 is, where necessary, pulverized and granulated to have appropriate particle size distribution according to a known pulverization granulation method. The average particle size of the granulated powder is preferably within the range of 0.1-40 μm, more preferably 0.5-30 μm. When the average particle size is not less than 0.1 μm, handling becomes easy and workability improves. On the other hand, when the average particle size is not more than 40 μm, the ceramic starting material is well dispersed in slurry 21 to easily afford a stable slurry.

Slurry 21 preferably maintains uniform dispersibility. To maintain uniform dispersibility of slurry 21, i.e., to improve dispersibility of slurry by increasing the viscosity of slurry 21, thereby consequently maintaining the form of a green body before sintering and further controlling the crystal grain growth during sintering, an additive may be used during slurry preparation. The additive is not particularly limited as long as it is a compound or composition capable of achieving the aforementioned object. The additive is preferably an organic product that burns during sintering. In this case, since a porous ceramic material obtained after sintering does not substantially contain a component derived from the additive, the material is superior in safety. Such an additive preferably contains one or more kinds of, for example, amino group, carboxyl group, carbonyl group and hydroxyl group. Specific examples thereof include monosaccharides (glucose, fructose, galactose, ribose, deoxyribose etc.), disaccharides (maltose, cellobiose, sucrose etc.), oligosaccharides and derivatives thereof, polysaccharides (cellulose, starch, amylopectin, chitin, chitosan, dextran etc.) and derivatives thereof (dextran ester etc.), polyethylene glycol, polyvinyl alcohol, gelatin, polylactic acid and the like. From the aspects of viscosity and dispersibility of the obtained slurry, preferred are polyethylene glycol, polyvinyl alcohol, gelatin, polylactic acid, polyacrylamide and salts thereof. In addition, these additives may be used in a combination of one or more kinds. Where necessary, a component other than the above-mentioned components may be added to slurry 21 within the range the object of the present invention is not inhibited.

Slurry 21 can be prepared according to a known method. Typically, slurry 21 can be prepared by adding a ceramic starting material and an additive while stirring water. Slurry 21 is preferably subjected to a defoaming treatment. In this case, air bubbles do not remain in the slurry and, as a result, undesirable pores (defect) caused by air babbles are not easily formed in a sintered body. For a defoaming treatment, a known method can be used and, for example, a defoaming method by stirring in vacuum, a defoaming method by planetary mixing and the like can be used.

FIG. 2(B) and FIG. 2(C) schematically show a step of freezing a slurry in a container (step B). In step B, the slurry 21 obtained in step A is filled in a container 31, and slurry 21 is unidirectionally frozen from one end of the container 31 to give a frozen body. As a specific method to unidirectionally freeze slurry 21, the vicinity of one end of the container 31 is intensively cooled to not more than the coagulation point the slurry 21. A specific apparatus therefor is to be mentioned below. As a result of such freezing, needle-like ice is grown and unidirectionally oriented in the compact. At this time, the circumference of the container 31 filled with the slurry 21 except the above-mentioned one end is cooled to a temperature higher than the coagulation point of the slurry 21. The white arrows in FIG. 2(C) schematically show cooling of the circumference of the slurry container 31 as mentioned above.

Figure 4:
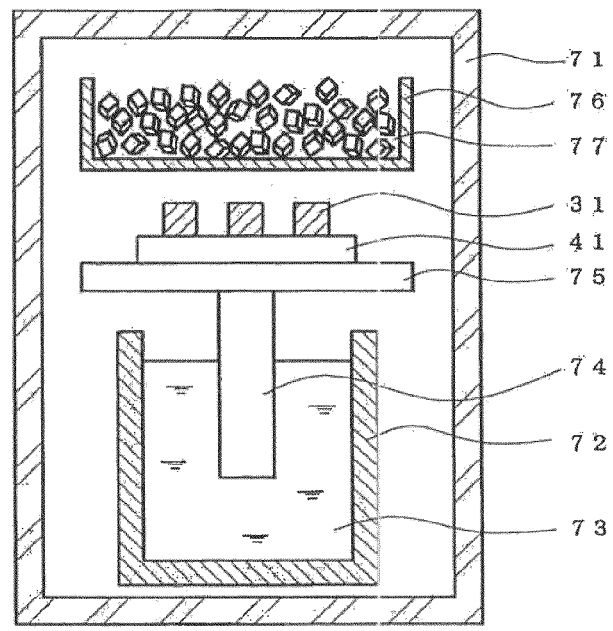
FIG. 4 is a schematic diagram of one example of a freezing apparatus to be used for freezing.

FIG. 4 is a schematic diagram of one example of a freezer apparatus to be used for freezing.

The aforementioned container 31 housing the slurry 21 is set on a sample table 41, the sample table 41 is set on a cooling plate 75, the cooling plate 75 is connected to a heat transfer rod 74 to be in contact with a cooling medium 73 such as liquid nitrogen and the like. The cooling medium 73 is placed in a cooling medium container 72. Above the container 31 is set a cooling apparatus 76, and the cooling apparatus 76 contains a cooling medium 77.

Using this freezer apparatus 71, the slurry is unidirectionally frozen from the side of the container 31 in contact with the sample table 41 to the upper direction. In a preferable embodiment of the present invention, one end of the container 31 is cooled to unidirectionally freeze the slurry, while cooling the circumference of the container 31 except the above mentioned one end. As a result of the aforementioned cooling, the temperature at 1 mm distant from the container 31 in the pore orientation direction becomes higher than the coagulation point of the slurry and not more than 15° C., more preferably higher than the coagulation point of the slurry and not more than 10° C., further preferably −15° C. to 5° C. The coagulation point of the slurry can be easily measured using a differential scanning calorimetry (DSC).

In this way, by cooling the circumference of the container 31 to a temperature higher than the coagulation point of the slurry 21 while unidirectionally freezing the slurry 21, the water contained in the slurry becomes long unidirectionally oriented columnar ice (needle-like ice), whereby a ceramic sintered body having unidirectionally long pores, with a small change in the cross sectional area in the pore orientation direction, can be obtained. In this case, the freezing rate of the slurry is preferably not more than 1.0 ml/min, more preferably not more than 0.1 ml/min.

The sample table 41 is preferably constituted with a metal having superior thermal conductivity such as brass, stainless steel and the like. To control the growth of the needle-like ice, the sample table 41 may be a sea-island structure type sample table obtained by partially filling a thermal insulation material having a lower thermal conductivity than that of the aforementioned metal plate. The method of producing such a sea-island structure type sample table is not particularly limited. For example, a method including forming a groove (concave) on the surface of a flat plate, filling the groove with a thermal insulation material having a low thermal conductivity such as an epoxy resin, and curing the same to give a sample table and the like can be employed. In addition, for forming a groove (concave) on the surface of a flat plate, a method including cutting processing a thermally conductive material plate such as a metal and forming a groove (concave) by pressing and etching the plate and the like can be employed.

The cooling medium 73 is not particularly limited as long as it can cool an end of the container 31 to a temperature not more than the coagulation point of the slurry. Specifically, alcohol, liquid nitrogen and the like can be mentioned. To control the cooling rate of a cooling surface and to keep the cooling temperature constant, the cooling medium may be additionally used as appropriate.

The container 31 is desirably formed from a thermal insulation material such as vinyl chloride resin, silicone resin, fluororesin and styrene resin so that the slurry will not freeze from the side wall of the container 31. The thickness of the side wall 33 of the container 31 is preferably not less than 0.5 mm. With this thickness, the contained slurry does not easily freeze from the side in contact with the side wall, and the structure of the needle-like ice unidirectionally arrayed becomes uniform.

All of the sample table 41, the cooling plate 75 and the heat transfer rod 74 or any optional two thereof are preferably integrally formed from a material superior in the thermal conductivity such as a metal, or they may be formed via a joint heterogeneous material having superior thermal conductivity. Since FIG. 4 is a schematic diagram, the diameter of the heat transfer rod 74 is not limited to the embodiment shown in the Figure. The heat transfer rod 74 may consist of a plurality of columnar members. When the heat transfer rod 74 is constituted with a plurality of columnar members, the cooling plate 75 and the sample table 41 can be more uniformly cooled.

Figure 3:
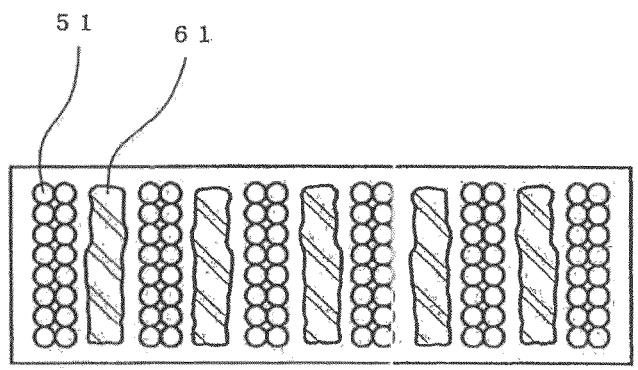
FIG. 3 is a schematic sectional view of a frozen slurry (FIG. 3A) and a green body (FIG. 3B).
Figure 3:
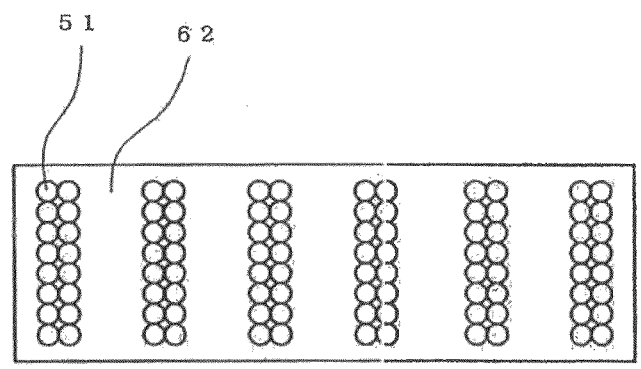

In step C, a green body is obtained by drying a frozen slurry. Typically, a container housing the slurry is freeze-dried under reduced pressure. By this operation, the needle-like ice is sublimated, and the place where the ice was present becomes pore. Consequently, unidirectionally oriented pores can be formed in the green body. FIG. 3 is a schematic sectional view of a frozen slurry (FIG. 3A) and a green body after drying (FIG. 3B). The frozen slurry contains particles 51, which are ceramic starting material, and substantially unidirectionally arrayed ice 61. After drying, pores 62 are formed in the region where the ice 61 was present.

In step D, the obtained green body is sintered. Typically, the green body obtained in step C is carefully extracted from the container 31, and sintered at a temperature and time suitable for each ceramic. For sintering (calcination), sintering conditions that impart the obtained sintered body with suitable mechanical strength for implantation, namely, the strength that enables processing at the actual clinical practice, and prevents breakage and the like after implantation, are desirably employed. Such sintering conditions can be appropriately determined in consideration of the kind of ceramics, porosity, average pore size, orientation of pores and the like. While the energy source to be used for sintering is not particularly limited, heat, microwave and the like are generally used.

In this way, a porous ceramic sintered body having pores of the sublimation trail of column-like ice can be prepared. The pores take the form of the aforementioned sublimation trail, and become continuous pores preferably unidirectionally penetrating the sintered body.

When the porous ceramic sintered compact of the present invention is used as a porous ceramic material such as artificial bone, it is preferably formed to have a desired shape and sterilized.

A method of forming into a block member is not particularly limited, and a known method can be used. Specific examples include a forming process by mechanical processing, a dry forming process, a wet forming process and the like. Since ceramic materials are generally hard and brittle, the conventional porous ceramic materials having uneven thickness of the ceramic layer showed extremely low machinability. As mentioned above, since the pores are unidirectionally oriented in the ceramic material of the present invention, and the pore size thereof is almost uniform, the thickness of the ceramic layer between pores is also almost uniform. Hence, the material shows superior machinability as compared to conventional porous ceramic materials.

In addition, the method for forming granules is not particularly limited, and a known method can be used. Specific examples include mechanical pulverization with a molder grinder, a ball mill, a jaw crusher, a hammer crusher and the like, pulverization in a mortar etc., and the like. In addition, the particle size of the pulverized porous ceramic material may be adjusted to be the same with a sieve and the like.

A method of sterilizing the material is not particularly limited, and a known method can be used. Specific examples include high-pressure vapor sterilization method (autoclave), gamma radiation sterilization, EOG sterilization, electron beam sterilization and the like. Of these, the high-pressure vapor sterilization method is widely used as a most common sterilization method.

A porous ceramic material obtained in this way has, as mentioned above, superior biocompatibility and sufficient strength for implantation, and is useful as a medical implant material such as artificial bone, artificial dental root and the like.

Furthermore, in an attempt to induce a bone tissue at a higher level, a substance having an action to promote growth of a bone tissue such as a transforming growth factor (TGF-$\beta 1$), osteoinductive factor, bone morphogenetic factor and the like may be impregnated in, adsorbed onto or immobilized onto the ceramic material of the present invention.

EXAMPLES

Slurry 21 obtained by dispersing or dissolving hydroxyapatite and gelatin as an additive in distilled water at the composition shown in Table 1 was filled in a vinyl chloride resin container 31 with a diameter of 16 mm and a height of 20 mm. Ten containers 31 were arranged on a sample table 41 on a discal cooling plate 75 with a diameter of 120 mm, cooled in a freezer 71 shown in FIG. 4 at a freezing rate of 0.015 ml/min to form needle-like ice in the slurry. The side of the freezer was cooled with a cooling medium such that the temperature near the slurry (temperature at 1 mm distant from the slurry container 31 in the orientation direction of the through-hole) becomes the temperature shown in Table 1. The thus-obtained frozen body was lyophilized in vacuum, and the green body was sintered at 1200° C. to give a ceramic material having oriented pores and high strength. The physical property thereof was measured by the aforementioned methods.

When the polyethylene glycol (average molecular weight about 600) permeation time was measured, a cylindrical test piece (diameter 3 mm×height 5 mm) was dipped in a polyethylene glycol (average molecular weight about 600) solution in the direction reverse to the cooling direction. When permeation of polyethylene glycol in the test piece was not observed even after elapse of 60 sec, the test was terminated, and evaluation of "not observed" was marked.

Machinability: the material was set on a lathe with the spindle rotation speed 3000 rpm, and cut with a diamond bite. When burr was visually observed, x was marked and when burr was not observed, ○ was marked.

Compressive strength test: JIS R 1608 was followed. The sample used was a cylindrical sample with diameter 5 mm×height 7.5 mm.

The production conditions and evaluation results of the ceramic materials of respective Examples and Comparative Examples are shown in Tables 1-3. In Table 2, the first sectional surface and the second sectional surface were both perpendicular to the pore orientation direction, and the distance between the both sectional surfaces was 5 mm.

TABLE 1

| | slurry composition | | | | |
|---|---|---|---|---|---|
| | calcium phosphate (HAp) | additive (gelatin) | water | temperature near slurry | freezing temperature |
| | | | | unit | |
| item | wt % | wt % | wt % | ° C. | ° C. |
| Example 1 | 17 | 4 | 79 | 2 | −15.6 |
| Example 2 | 13 | 4 | 83 | 2 | −14.2 |
| Example 3 | 17 | 4 | 79 | 5 | −15.6 |
| Example 4 | 17 | 4 | 79 | 0 | −15.6 |
| Example 5 | 17 | 4 | 79 | −5 | −15.6 |
| Comparative Example 1 | 17 | 4 | 79 | −25 | −15.6 |
| Comparative Example 2 | 17 | 4 | 79 | 20° C. (without cooling) | −15.6 |

TABLE 2

| | physical property of sintered body | | | |
|---|---|---|---|---|
| | | | item | |
| | | | | average open area of pore |
| | porosity | pore length along the orientation direction | first sectional surface | second sectional surface |
| | | | unit | |
| | % | mm | ×10$^{-3}$ mm$^2$ | ×10$^{-3}$ mm$^2$ |
| Example 1 | 82 | 10 | 16.1 | 4.6 |
| Example 2 | 86 | 10 | 15.2 | 5.3 |
| Example 3 | 82 | 5 | 29.2 | 5.0 |
| Example 4 | 82 | 15 | 12.5 | 3.7 |
| Example 5 | 82 | 15 | 7.5 | 3.4 |
| Comparative Example 1 | 82 | no pore | — | — |
| Comparative Example 2 | 82 | 2 | 365 | 5.0 |

TABLE 3

| | physical property of sintered body item | | |
|---|---|---|---|
| | polyethylene glycol permeation time | | compressive strength |
| | unit | | |
| | sec | machinability | MPa |
| Example 1 | 5 | o | 8.63 |
| Example 2 | 3 | o | 2.97 |
| Example 3 | 5 | o | 5.79 |
| Example 4 | 3 | o | 4.62 |
| Example 5 | 2 | o | 5.47 |
| Comparative Example 1 | not observed | x | 3.13 |
| Comparative Example 2 | not observed | x | 1.02 |

Figure 8:
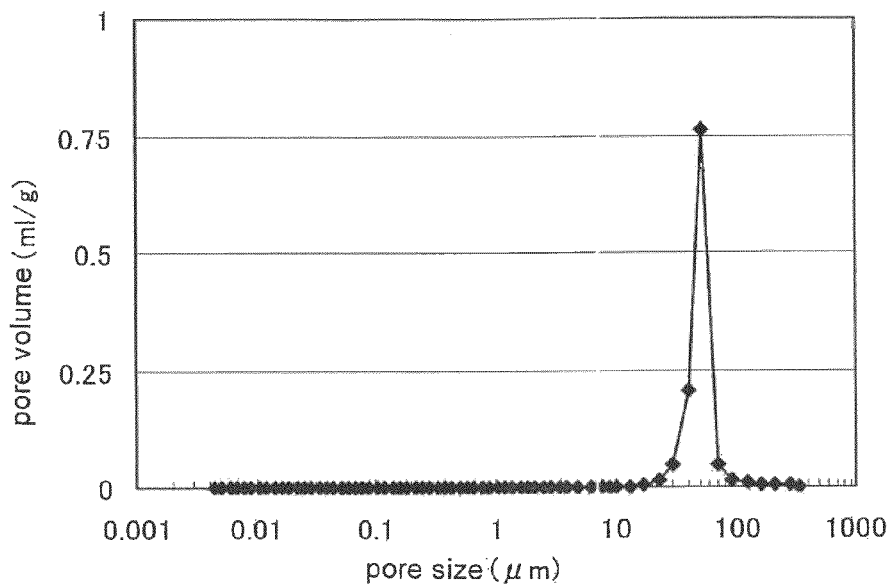
FIG. 8 is a view showing the pore size distribution of the material of Example 1.

The porous ceramic material produced in Example 1 was measured for the pore size distribution according to the mercury porosimetry. The test method followed JIS R 1655:2003. FIG. 8 shows the experimental results obtained in this test. From FIG. 8, it can be confirmed that the porous ceramic material of the present invention shows pore size distribution with a single peak near pore size 50 μm and no peak at pore size of not more than 0.1 μm, and that ceramic particles had been densely sintered.

Figure 5:
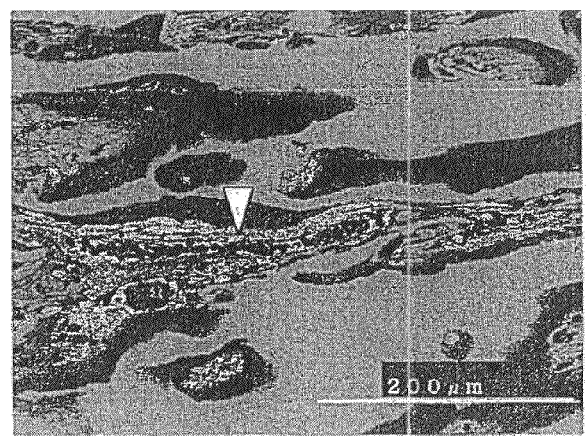
FIG. 5 is a light micrograph of a tissue section at 4 weeks after implantation into a rabbit femur.

A hole with diameter 5 mm×height 10 mm was made in the distal femur of 12-week-old healthy male SPF rabbit by drilling from the knee joint. Furthermore, the porous ceramic material produced in Example 1 was formed into a diameter 4 mm×height 6 mm piece, which was implanted in the pore with diameter 5 mm×height 10 mm produced in the femur. The periostea•subcutaneous tissue and the skin were sutured and closed. At 4 weeks from the implantation, the implanted site was harvested, and fixed with 10% neutral buffered formalin. After fixing, the implanted site was semi-decalcificated by an ion exchange resin method, and morphologically evaluated. FIG. 5 is a light micrograph of the tissue section obtained by the above-mentioned experiment. In the Figure, ∇ shows the part where a capillary blood vessel-like tissue was observed in the pore.

Figure 6:
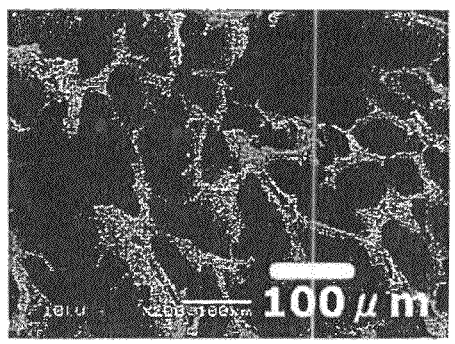
FIG. 6 is an SEM observation image of a cross section of the material of Example 1.
Figure 6:
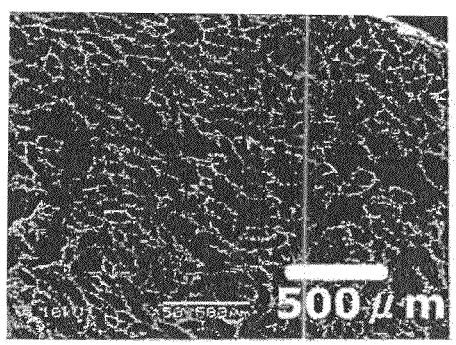
Figure 6:
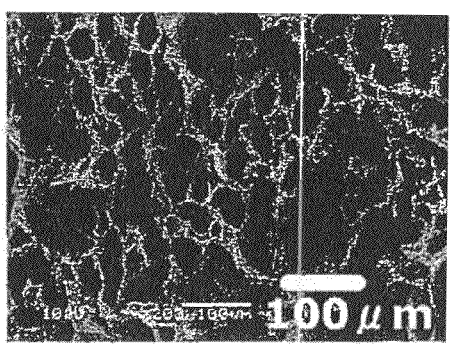

FIG. 6 shows an SEM observation image of the cross section of the material of Examples 1. FIGS. 6(A) and 6(B) show observed images (with different magnifications) of cross section perpendicular to the pore orientation direction, and FIG. 6(C) shows an observed image of a cross section parallel to FIGS. 6(A) and 6(B) and about 10 mm distant therefrom.

Figure 7:
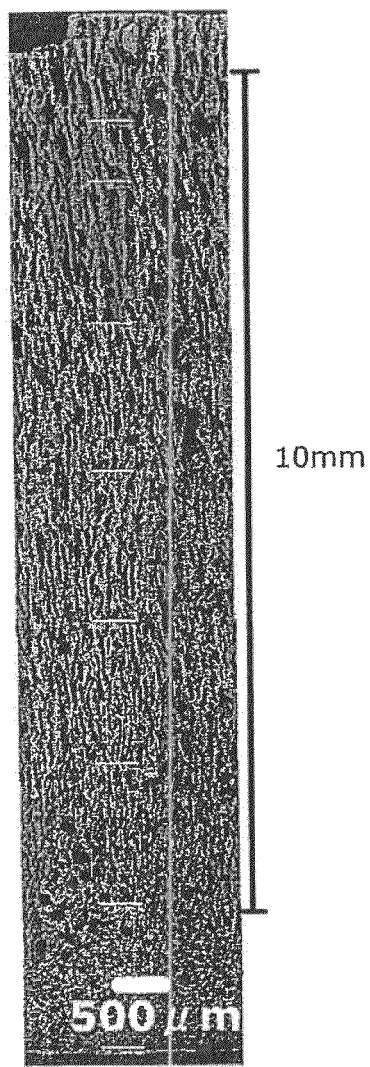
FIG. 7 is an SEM observation image of a cross section of the material of Example 1.

FIG. 7 shows an SEM observation image of the cross section of the material of Example 1. In FIG. 7, plural observation images of the cross section parallel to the pore orientation direction. FIG. 7 reveals the presence of pores having a length of not less than about 10 mm.

Figure 9:
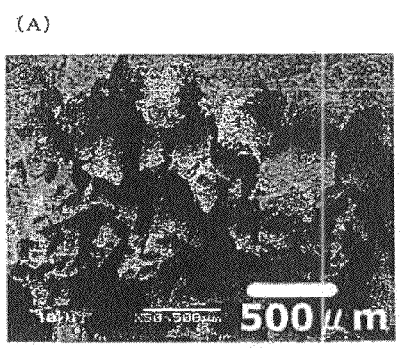
FIG. 9 is an SEM observation image of a cross section of the material of Comparative Example 2.
Figure 9:
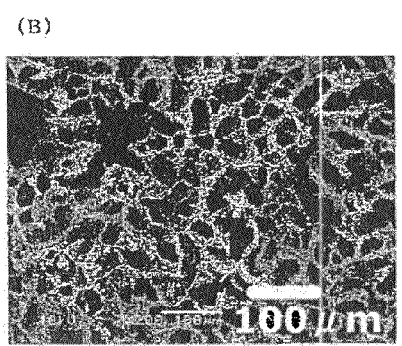

FIG. 9 shows an SEM observation image of the cross section of the material of Comparative Example 2. FIG. 9(A) shows an observed image of the same cross section perpendicular to the pore orientation direction, and FIG. 9(B) shows an observed image of the cross section parallel to FIG. 9(A) and about 4 mm distant therefrom. While FIG. 9(B) confirms the presence of pores, FIG. 9(A) hardly reveals a pore structure.

Figure 10:
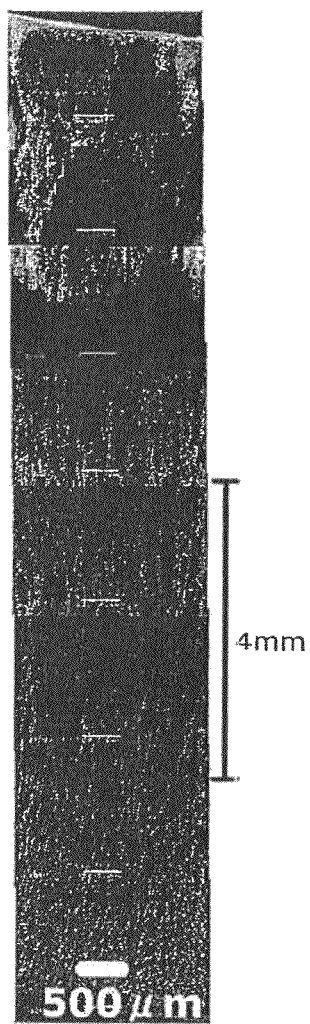
FIG. 10 is an SEM observation image of a cross section of the material of Comparative Example 2.

FIG. 10 is an SEM observation image of the cross section of the material of Comparative Example 2. In FIG. 10, plural observation images of the cross section parallel to the pore orientation direction have been connected. According to FIG. 10, the length of the pores is only about 4 mm.

This application is based on a patent application No. 2006-174372 filed in Japan, the contents of which are incorporated in full herein by this reference.

The invention claimed is:

1. A porous ceramic material having a porosity of 82-90% and a compressive strength according to JIS R 1608 of from 2.97 to 8.63 MPa, and having substantially unidirectionally oriented pores in its inside, wherein when a cylindrical test piece consisting of the porous ceramic material having dimensions of diameter 3 mm×height 5 mm, and wherein the pore orientation direction is in a height direction, is dipped in polyethylene glycol up to 1 mm from one end thereof, polyethylene glycol permeates through the whole test piece within 30 seconds.

2. The porous ceramic material of claim 1, comprising calcium phosphate as a main component.

3. The porous ceramic material of claim 2, wherein the calcium phosphate is hydroxyapatite and/or tricalcium phosphate.

4. A porous ceramic implant material comprising the porous ceramic material of claim 3.

5. A porous ceramic implant material comprising the ceramic material of claim 2.

6. A porous ceramic implant material comprising the porous ceramic material of claim 1.

7. The porous ceramic material of claim 1, which is sintered.

8. The porous ceramic material of claim 1, which is sintered at a temperature of 1200° C.

9. A porous ceramic material having (a) substantially unidirectionally oriented pores, (a1) a compressive strength according to JIS R 1608 of from 2.97 to 8.63 MPa, (b) a porosity of 82-90%, and (c) an average cross sectional area of one pore of $0.05 \times 10^{-3}$-$50 \times 10^{-3}$ mm$^2$ both in a first sectional surface perpendicular to the pore orientation direction and a second sectional surface parallel to the first sectional surface and 5 mm distant from the first sectional surface in the pore orientation direction.

10. The porous ceramic material of claim 9, comprising calcium phosphate as a main component.

11. The porous ceramic material of claim 10, wherein the calcium phosphate is hydroxyapatite and/or tricalcium phosphate.

12. A porous ceramic implant material comprising the porous ceramic material of claim 11.

13. A porous ceramic implant material comprising the porous ceramic material of claim 10.

14. A porous ceramic implant material comprising the porous ceramic material of claim 9.

* * * * *